(12) United States Patent
Doyle

(10) Patent No.: US 7,446,317 B2
(45) Date of Patent: Nov. 4, 2008

(54) MULTIPASS CELL FOR GAS ANALYSIS USING A COHERENT OPTICAL SOURCE

(75) Inventor: Walter M. Doyle, Laguna Niguel, CA (US)

(73) Assignee: Axiom Analytical, Inc., Tustin, CA (US)

(*) Notice: Subject to any disclaimer, the term of this patent is extended or adjusted under 35 U.S.C. 154(b) by 81 days.

(21) Appl. No.: 11/671,364

(22) Filed: Feb. 5, 2007

(65) Prior Publication Data

US 2007/0187607 A1 Aug. 16, 2007

Related U.S. Application Data

(60) Provisional application No. 60/764,479, filed on Feb. 3, 2006.

(51) Int. Cl.
*G01N 21/61* (2006.01)
(52) U.S. Cl. .......... 250/343; 250/339.13; 250/574; 250/577; 250/576; 356/246; 356/301; 356/311
(58) Field of Classification Search ......... 250/343, 250/339.13, 574, 576, 577; 356/246, 301, 356/311
See application file for complete search history.

(56) References Cited

U.S. PATENT DOCUMENTS

| | | | | |
|---|---|---|---|---|
| 3,704,951 A | * | 12/1972 | Chupp | 356/301 |
| 5,440,143 A | * | 8/1995 | Carangelo et al. | 250/573 |
| 5,459,566 A | * | 10/1995 | Pearson et al. | 356/246 |
| 5,485,276 A | * | 1/1996 | Bien et al. | 356/437 |
| 5,731,583 A | * | 3/1998 | Bailey et al. | 250/343 |
| 5,949,537 A | * | 9/1999 | Inman et al. | 356/246 |
| 6,844,553 B2 | * | 1/2005 | Daly et al. | 250/339.07 |
| 2003/0081206 A1 | * | 5/2003 | Doyle | 356/301 |
| 2004/0004720 A1 | * | 1/2004 | Cliche et al. | 356/440 |
| 2006/0158644 A1 | * | 7/2006 | Silver | 356/246 |
| 2006/0232772 A1 | * | 10/2006 | Silver | 356/246 |

* cited by examiner

*Primary Examiner*—David P. Porta
*Assistant Examiner*—Djura Malevic
(74) *Attorney, Agent, or Firm*—Myers Dawes Andras & Sherman LLP; Joseph C. Andras

(57) ABSTRACT

A multi-pass gas cell that operates with reflected radiation pass through a gas, the reflected radiation transmitted and received by first and second fiber optic ports that are subject to an alignment adjustment, and a mirrored viewing window having a inner reflective surface exposed to an interior of the elongated cell body for reflecting the radiation within the cell body, an outer viewing surface, and a transmittance characteristic that permits a portion of the radiation to pass through the mirrored window, from the inner reflective surface to the outer viewing surface, as a visual indicator of the alignment condition of the reflected radiation relative to the first and second fiber-optic ports.

8 Claims, 5 Drawing Sheets

US 7,446,317 B2

MULTIPASS CELL FOR GAS ANALYSIS USING A COHERENT OPTICAL SOURCE

PRIORITY CLAIM

This patent application claims the benefit of U.S. Provisional Patent Application Ser. No. 60/764,479, filed on Feb. 3, 2006, and entitled MULTIPASS CELL FOR GAS ANALYSIS USING A COHERENT OPTICAL SOURCE, pursuant to 35 USC 119. The entire contents of this provisional patent application are hereby expressly incorporated by reference.

BACKGROUND OF THE INVENTION

1. Field of the Invention

The present invention is generally directed to instruments used for spectroscopic analysis and more particularly to a multipass cell for gas analysis using a coherent optical source.

2. Description of the Related Art

Multipass cells are commonly used in the spectroscopic analysis of gases. The basic idea involves folding the path followed by the optical radiation so that it crosses the same volume of gas multiple times. This maximizes the optical pathlength while minimizing cell volume and physical size. Until recently most spectroscopic gas analysis was performed with incoherent radiation such as the modulated infrared radiation present in the sample region of an FTIR spectrometer. The cells used have typically been of the White cell type (see FIG. 1).

When using a White cell, the incoherent radiation is focused on the input aperture of the cell. (In FIG. 1, this is shown as a small reflector). After passing through this, it expands to a relatively large diameter where it is intercepted by a correspondingly large, curved reflector. This re-condenses the radiation to form an image roughly in the same plane as the input aperture. By using two large condensing curved mirrors and a third curved mirror between the input and output apertures, as illustrated, it is possible to arrange for multiple passes. In this design, the radiation is successively imaged at points along one or two lines on the mirror between the apertures. After a predetermined number of passes, the radiation leaves the cell through a second aperture.

An object of the invention, therefore, is to provide a multipass gas cell for use with a coherent (tunable laser) spectrometer that can be taken apart for cleaning and then reassembled and easily realigned.

BRIEF SUMMARY OF THE INVENTION

In one aspect, the invention may be regarded as a multipass gas cell comprising: a cell body configured for allowing a gas to be analyzed to pass therethrough under high pressure, high temperature, or both; a first fiber-optic port for transmitting radiation into the cell body; means for adjusting an alignment condition of the fiber-optic input; a mirrored window having a inner reflective surface exposed to an interior of the elongated cell body for reflecting the radiation within the cell body; a second fiber optic port for receiving the radiation reflected by the mirrored window and outputting it for analysis; and the mirrored window further having an outer surface and a transmittance characteristic that permits a portion of the radiation to pass through the mirrored window as a visual indicator of the alignment condition of the reflected radiation relative to the first and second fiber-optic ports.

While the apparatus and method has or will be described for the sake of grammatical fluidity with functional explanations, it is to be expressly understood that the claims, unless expressly formulated under 35 USC §112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC §112 are to be accorded full statutory equivalents under 35 USC §112. The invention can be better visualized by turning now to the following drawings wherein like elements are referenced by like numerals.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION OF THE PREFERRED EMBODIMENTS

In developing my invention, I attempting to solve the problem of designing, multipass gas cell that would withstand high temperatures and pressures, that would be extremely chemically inert, and that could be periodically dissembled for cleaning. The cleaning requirement implied that I would have to provide a means for aligning the cell after it was reassembled.

Figure 1:
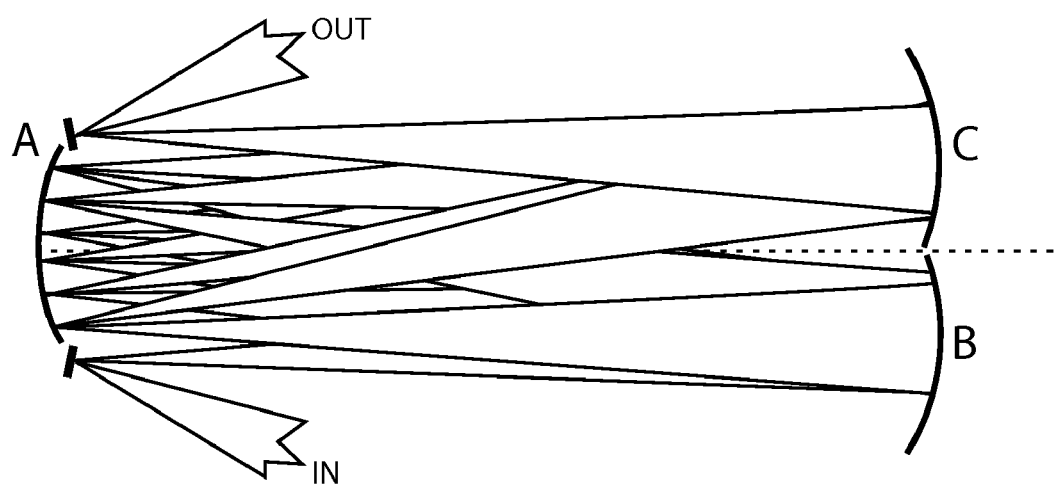
FIG. 1 shows a prior art White cell which are sometimes made with a cell body formed of a transparent material such as glass so that a laser can be used to visually trace to path in the cell, but such cells, of course, are not suitable for high pressure operation.
Figure 2:
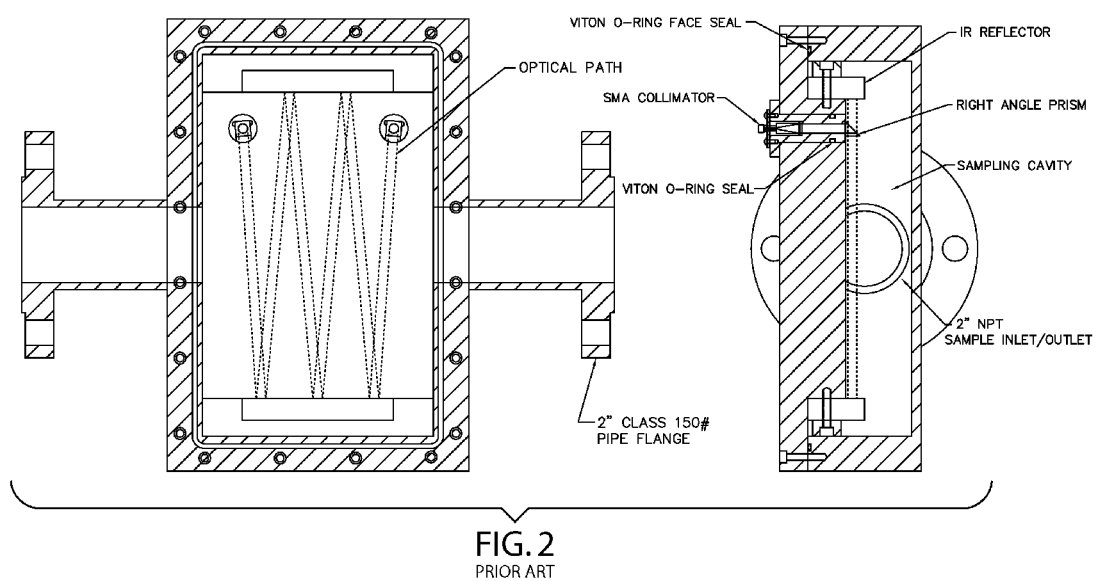
FIG. 2 shows a prior art gas cell of rectangular cross section where one side of the cell can be removed for alignment.

One approach to providing for alignment of an assembled gas cell is to fabricate the cell body from a transparent material such as glass. A visible light source such as a laser can then be used to visually trace to path in the cell. This approach is used for many commercial White cells. However, it is not suitable for high pressure operation. A second approach is to use a rectangular cross section so that one side of the cell can be removed for alignment. This approach was used for an early version of our gas cell. (See FIG. 2.) However, it rapidly becomes impractical as the length of the cell is increased.

The solution to this problem was made possible by the fact that the gas cell to be designed was to operate with a spectrometer based on a tunable laser as the radiation source. As a result, the radiation within the cell could be made highly collimated, and it would not be necessary to use curved mirrors to refocus the radiation as is done in the White cell design.

The key element of my invention is the use of at least one optical element that serves both as a mirror and a window so that the position of the optical beam, on reflection, can be viewed from outside of the cell.

Figures 3B, 4B:
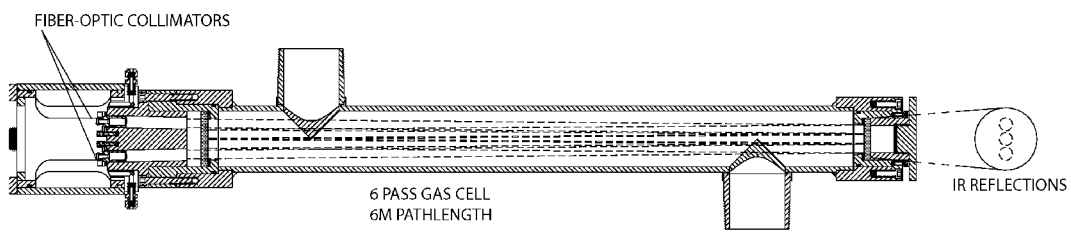
FIG. 3B shows a 6-pass gas cell according to a second preferred embodiment of the invention where a viewing mirror at the far end of the cell is designed in such a way as to allow at least partial viewing of a visible laser beam which strikes it multiple times.
FIGS. 4A and 4B show the patterns of reflecting areas that would be appropriate for a cell that provides two passes (FIG. 3A) or six passes (FIG. 3B), respectively.
Figures 3A, 4A:
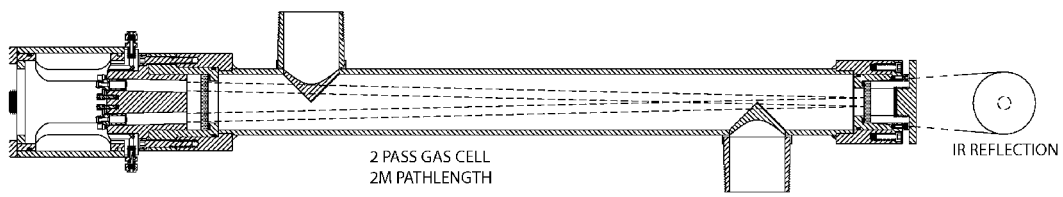
FIG. 3A shows a 2-pass gas cell according to a preferred embodiment of the invention where a viewing mirror at the far end of the cell is designed in such a way as to allow at least partial viewing of a visible laser beam which strikes it once.

A preferred embodiment of my invention is shown in the gas cells of FIGS. 3A and 3B. FIG. 3A shows a gas cell with a body length and an input/output end having fiber-optic collimators configured to provide two passes, and FIG. 3B shows a gas cell with a body length and input/output end configured to provide six passes.

In either case, the optical signal from the laser source reaches the cell through a single mode optical fiber, i.e. a fiber having a very small core diameter (typically 0.009 mm). A collimating lens is used to collect the light emerging form the fiber and form it into a collimated beam. After some number of passes back and forth through the cell (e.g. 2, 4, 6, etc.), the light is collected by a second lens and focused on a second optical fiber. This collection fiber will generally have a much larger core diameter (typically 0.6 mm). In my design, the ends of the cell are provided with flat reflecting surfaces.

The collimated beam is simply reflected between these surfaces until it reaches the second lens. The number of passes through the cell is determined by the angles of the two collimating lens assemblies. Fine adjustment of these angles also serves to align the cell so as to maximize the transmitted signal for a given number of reflections.

In the embodiments shown in FIGS. 3A and 3B, both the transmitting and receiving lens assemblies are located at one end of the cell and connected to suitable means for adjusting their alignment condition. The mirror at the far end of the cell is then designed in such a way as to allow at least partial viewing of a visible laser beam which strikes it. (Note that, although the cell may be operated in the near infrared region of the spectrum, a visible laser can still be used for all but the final fine tuning of the alignment.)

Two approaches are possible for the design of the viewing mirror. The first involves making only certain portions of the surface reflective.

FIGS. 4A and 4B show the patterns of reflecting areas that would be appropriate for a cell that could provide either two passes (FIG. 3A) or six passes (FIG. 3B), respectively. The diameter of each reflecting spot needs to be only slightly larger than that of the receiving lens. However there will be an inherent, albeit slight, divergence of the beam due to the finite size of the input fiber and the inevitable aberrations of the optics. As a result, some light may get by the mirrored spots even when the cell is optimally aligned. When the cell is misaligned, even more light will bypass the mirrors. The distribution of the optical beam can be viewed by placing a translucent target outside of the mirrored window.

In addition to providing for alignment, the embodiment just described has a second benefit in that it allows the inside of the window—and to some extent other areas of the cell—to be inspected for contamination.

Figure 5:
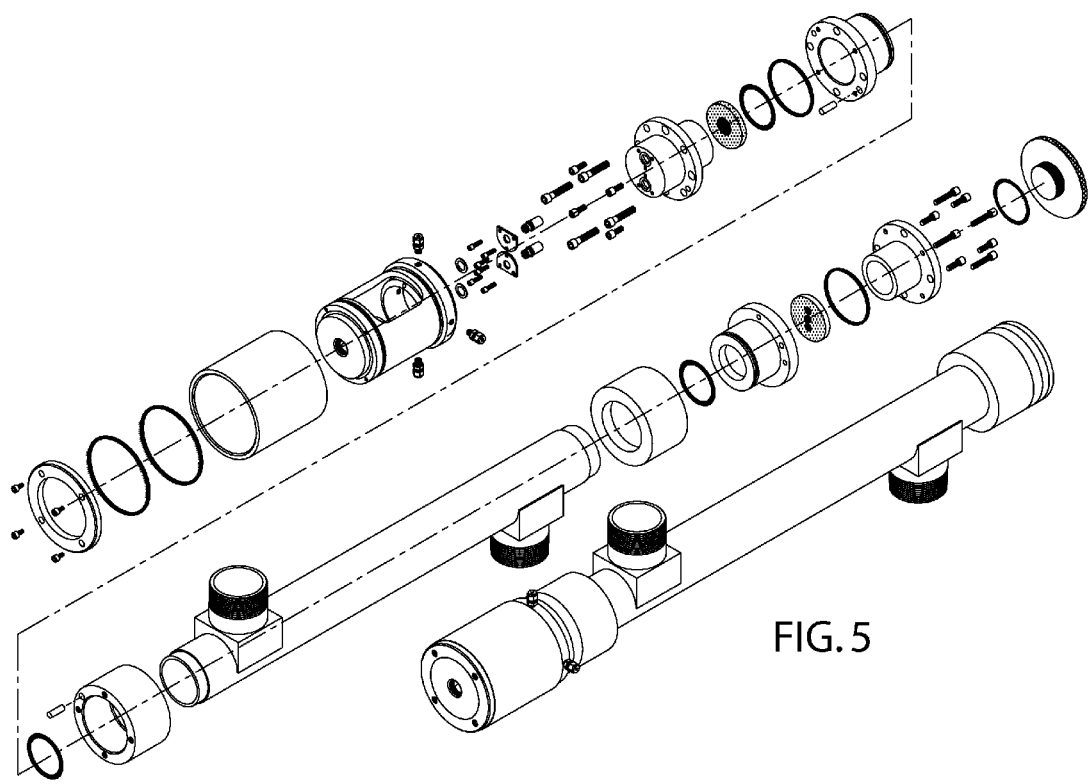
FIG. 5 is an exploded perspective view of a presently preferred gas cell made according to a first embodiment of the invention.

FIG. 5 is an assembly drawing of a commercial gas cell based on my invention. In this case, the mirrored window (Item 25) has a single reflecting spot in its center, providing two optical passes through the cell. Angular adjustment of the fiber-optical collimators (Items 12) is provided by the clamp (Item 9) and Belleville washer (Item 23).

A second embodiment of my invention involves providing a mirrored surface which is highly reflecting in the spectral range being used for analysis but somewhat less reflecting at the frequency of the visible alignment laser so that a portion of the laser beam can pass through the mirror and be viewed. In this case the whole surface of the window can be coated. For a substantial number of reflections, it would be necessary to keep the transmittance of the window quit low so that the alignment beam is still strong enough to be viewed after several passes. This will make the design less useful for cell inspection than the design of FIG. 4.

Figure 6:
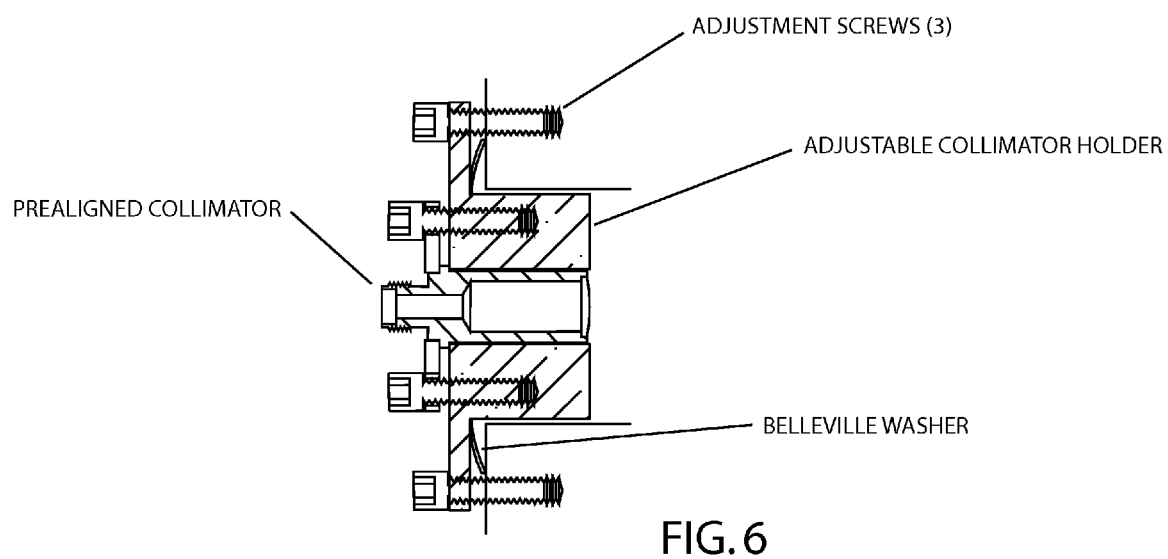
FIG. 6 shows a collimator comprised of an outer assembly which provides angular adjustment and an interchangeable inner assembly that has a fixed focus optimized for a specified wavelength range.

A potential problem with the embodiments describe above results from the chromatic aberration of the collimating lens. If the collimator is designed for optimum transmission in the near infrared region, it will be somewhat out of focus for visible radiation. Although such problems are generally solved by using an achromatic lens, it may not be possible to obtain a suitable achromat which covers the full spectral range required. An alternative approach is shown in FIG. 6. Here, the full collimator assembly is comprised of two parts, an outer assembly which provides angular adjustment and interchangeable inner assemblies. Each of the inner assemblies can have a fixed focus optimized for a specified wavelength range. The inner assemblies will need to have their lenses precisely centered so that they can be interchanged without significantly effecting angular alignment.

What is claimed is:

1. A multi-pass gas cell comprising:
   a cell body configured for allowing a gas to be analyzed to pass therethrough under high pressure, high temperature, or both;
   a first fiber-optic port for transmitting radiation into the cell body;
   means for adjusting an alignment condition of the fiber-optic input;
   a mirrored window having a inner reflective surface exposed to an interior of the elongated cell body for reflecting the radiation within the cell body;
   a second fiber optic port for receiving the radiation reflected by the mirrored window and outputting it for analysis; and
   the mirrored window further having an outer surface and a transmittance characteristic that permits a portion of the radiation to pass through the mirrored window as a visual indicator of the alignment condition of the reflected radiation relative to the first and second fiber-optic ports.

2. The multi-pass gas cell of claim 1 wherein the mirrored window comprised a reflecting spot that corresponds to an aligned condition of the fiber-optic input.

3. The multi-pass gas cell of claim 2 wherein the reflecting spot is a single reflecting spot located in the center of the mirrored window.

4. The multi-pass gas cell of claim 1 wherein the mirrored window has the whole of its inner reflective surface coated with a reflective coating that is partially transmissive.

5. The multi-pass gas cell of claim 1 wherein the radiation used for alignment is different then the radiation used for measurement.

6. The multi-pass gas cell of claim 1 wherein the radiation used for alignment is a coherent laser beam.

7. The multi-pass gas cell of claim 6 wherein the first and second fiber-optic ports are formed from an outer assembly comprising an adjustable collimator holder and an inner, interchangeable assembly comprising a collimator lens.

8. The multi-pass gas cell of claim 7 wherein a first inner assembly is used for coherent radiation suitable for visual alignment and wherein a second inner assembly is used with radiation suitable for analysis.

* * * * *